United States Patent [19]
Zallie et al.

[11] Patent Number: 5,480,669
[45] Date of Patent: Jan. 2, 1996

[54] METHOD FOR INCREASING EXPANSION AND IMPROVING TEXTURE OF FIBER FORTIFIED EXTRUDED FOOD PRODUCTS

[75] Inventors: James P. Zallie, Hillsborough; Paul A. Altieri, Belle Mead; Chung-Wai Chiu, Westfield; Matthew Henley, Somerville, all of N.J.

[73] Assignee: National Starch and Chemical Investment Holding Corporation, Wilmington, Del.

[21] Appl. No.: 217,784

[22] Filed: Mar. 24, 1994

Related U.S. Application Data

[63] Continuation-in-part of Ser. No. 36,603, Mar. 24, 1993, abandoned.

[51] Int. Cl.$^6$ ............................. A21D 2/36; A23L 1/0522
[52] U.S. Cl. ........................... 426/549; 426/516; 426/557; 426/560; 426/578; 426/661
[58] Field of Search ..................................... 426/549, 661, 426/578, 516, 18, 518, 557, 560

[56] References Cited

U.S. PATENT DOCUMENTS

| | | | |
|---|---|---|---|
| 4,423,082 | 12/1983 | Bauerfeind | 426/557 |
| 5,051,271 | 9/1991 | Iyengar et al. | 426/658 |
| 5,151,283 | 9/1992 | Foehse et al. | 426/93 |
| 5,169,662 | 12/1992 | Spicer | 126/449 |
| 5,176,936 | 1/1993 | Creighton et al. | 426/618 |
| 5,281,432 | 1/1994 | Zallie et al. | 426/661 |

FOREIGN PATENT DOCUMENTS

| | | |
|---|---|---|
| 0512249 | 11/1992 | European Pat. Off. . |
| 0529894 | 3/1993 | European Pat. Off. . |
| 9015147 | 12/1990 | WIPO . |
| WO93/03629 | 3/1993 | WIPO . |

OTHER PUBLICATIONS

Ca. Inst. Food Sci. Technol. J. vol. 17, No. 2, pp. 65–70, 1984 *Textural and Microstructural Changes in Corn Starch as a Function of Extrusion Variables*, J. Owusu–Ansah, et al.
Cereal Chem. 61(2):174–179 *Extrusion Cooking and Dietary Fiber: Effects on Dietary Fiber Content and on Degradation in the Rat Intestinal Tract*, I. Bjorck, et al.
Journal of Cereal Science 4 (1986) 315–323, *The Effects of Various Thermal Processes on Dietary Fibre and Starch Content of Whole Grain Wheat and White Flour*, M. Siljestrom, et al.
Cereal Chemistry, vol. 52, May–Jun. 1975, No. 3, part I, pp. 283–297 *Modification of Carbohydrate Components by Extrusion–Cooking of Cereal Products*, C. Mercier, et al.
Cereal Chem. 65(2):138–143, *Relationship Between Amylose Content and Extrusion–Expansion Properties of Corn Starches*, R. Chinnaswamy, et al.
Lecture presented at the 27th Starch Convention of the Arbeitsgemeinschaft Getreideforschung in Germany from Apr. 28 to 30, 1976, *Effect of Extrusion–Cooking on Potato Starch Using a Twin Screw French Extruder*, C. Mercier.
Cereal Sci. Today, Sep. 1973, vol. 18, No. 9, p. 286, *Changes in Various Starches by Cooking-Extrusion Processing: II Physical Structure of Extruded Products*.
Journal of Food Science, vol. 58, No. 6, 1992, *Raw–Starch Degrading Amylase(s) Affect Enzyme–Resistant Starch*, pp. 1443–1444, L. Gruchala, et al.
Cereal Foods World, May 1989, vol. 34, No. 5, *Microstructural, Physicochemical, and Macromolecular Changes in Extrusion–Cooked and Retrograded Corn Starch*, R. Chinnasawamy, et al.
Journal of Food Science, vol. 48, (1983), *Changes in Starch Fraction During Extrusion–Cooking of Corn*, M. H. Gomez et al.
Cereal Chemistry, vol. 61, No. 6, 1984, *Extrusion Cooking and Drum Drying of Wheat Starch. I. Physical and Macromolecular Modifications*, P. Colonna, et al.

*Primary Examiner*—Helen Pratt
*Attorney, Agent, or Firm*—Jane E. Gennaro

[57] ABSTRACT

A method to increase the fiber content of extruded foods by the addition of resistant starch to starting dough mixes for extruded food products which increases the total dietary fiber of the extruded food product, and also increases expansion and improves the texture of the extruded food over compositions that do not contain the resistant starch and over compositions that are fortified with other forms of dietary fiber, such as oat bran or wheat bran.

4 Claims, No Drawings

METHOD FOR INCREASING EXPANSION AND IMPROVING TEXTURE OF FIBER FORTIFIED EXTRUDED FOOD PRODUCTS

This application is a continuation-in-part of application Ser. No. 08/036,603 filed 24 Mar. 1993, now abandoned.

FIELD OF THE INVENTION

This invention is a method for increasing the expansion or improving the texture of food products that are prepared by extrusion techniques and that are fortified with dietary fiber.

BACKGROUND OF THE INVENTION

Cereals constitute a major part of the human diet and are an important source of starch and dietary fiber. In the preparation of cereals for human consumption high temperature-short time extrusion cooking is widely used. The food products prepared by extrusion techniques are typically ready-to-eat cereal and snack foods, crisp breads, pasta and noodles. Research literature has indicated that the inclusion of fiber into human diets is beneficial, and as a result, there have been attempts to fortify extruded foods with dietary fiber. Nevertheless, it has proven difficult to make a satisfactory food product that has high fiber content through extrusion techniques.

The quality attributes of extruded food products pertain mainly to their texture and crispness, which in turn relate to their expanded volume and bulk density. It is known that extrusion processing variables, such as, barrel temperature, screw configurations, nozzle size and shape, screw speed, and moisture content prior to thermal processing, can influence the expansion volume of the extruded product. The protein, lipid, and starch content of the raw materials for making the dough mix also affect the texture and expansion volume of extruded foods.

In U.S. Pat. Nos. 5,169,662 and 5,176,936, it is disclosed that products with significant amounts of dietary fiber are difficult to expand. Expansion is critical in certain extruded foods because the crispness and texture of the foods is related to expanded volume and bulk density. It is also difficult to obtain good or acceptable texture in flaked products or in pasta and noodles when those products are fortified with high fiber because the addition of dietary fiber adds density and reduces favorable texture and overall eating quality.

SUMMARY OF THE INVENTION

This invention is a method to fortify extruded food products with dietary fiber without compromising texture and crispness. Fortification is accomplished with the addition of resistant starch, which is starch resistant to amylase digestion, to the uncooked dough mix. Resistant starch is considered to be dietary fiber as analyzed by the AOAC method of determining dietary fiber (Association of Official Analytical Chemists) (Prosky et al.). The addition of resistant starch to dough compositions that are intended to be cooker extruded will yield a fiber fortified food product that has increased expansion over food products that do not contain the resistant starch or that are fortified with other forms of dietary fiber, such as oat bran. For those foods that are intended to be extruded and then compressed or flaked, the addition of resistant starch results in improved texture over food products that do not contain the resistant starch or that are fortified with other forms of dietary fiber. When used in pasta, the addition of resistant starch results in a fiber fortified pasta without any substantial loss in firmness and a better overall eating quality compared to the addition of other forms of fiber.

DETAILED DESCRIPTION OF THE INVENTION

The increase in expansion of extruded food products is obtained by preparing a dough from uncooked cereal ingredients, which includes resistant starch in amounts up to 45% by weight, preferably 10–25%, with sufficient water to attain a moisture content of 14–22% by weight, preferably 15–17% by weight. This dough is then cooked in an extruder through varied temperature zones, usually ranging from 60°–170° C., over a short time period, usually about 0.2–1.5 minutes. The extruding process will usually occur at pressures in the range of $2\times10^6$–$4.3\times10^6 \text{N/m}^2$ (Pa). The temperatures, pressures, and time for cooking can be optimized for each individual dough composition and this optimization is within the expertise of one skilled in the art. The cooked dough exits a die, chosen by size and shape in relation to the desired size and shape of the extruded food product. The choice of the particular die is within the expertise of one skilled in the art. The pressure at the die typically ranges from $1.38\times10^6$–$6.21\times10_6 \text{N/m}^2$ (PA) (200–900 psi), and can be varied for optimization of the process. The expansion of the moisture within the dough as it exits the extruder from a zone of high pressure to a zone of low pressure results in the formation of the expanded food product. The addition of resistant starch to the dough mix can increase this expansion significantly, in some compositions, for example, up to 60%, compared to other high fiber formulas.

For expanded food products, the extrusion parameters are chosen so that the extrudate exits the extruder with a moisture content of approximately 8–11% by weight. In order to prolong stability, the extruded products generally are dried after extrusion to a final moisture content of less than 3%, since greater moisture content reduces the shelf life of the product. Drying can be accomplished by oven drying or belt drying, or any other drying technique that is known and used in the art.

For those food products that are intended to be delivered as flakes, an improvement in texture is obtained by adding up to 45% by weight, preferably 10–25%, resistant starch to the uncooked cereal dough, with sufficient water to attain a moisture content of about 30% by weight, although lower moisture content may be used. In this case, the temperatures and pressures will be somewhat lower than for expanded food products and the optimization of extrusion parameters is within the expertise of those skilled in the art. Generally, the dough is processed within varied temperature zones from 60°–170° C., and at pressures in the range of $1.7\times10^6$–$2.2\times10^6 \text{N/m}^2$ (PA). An appropriate exit die is chosen to extrude the dough as a rope, which is then cut into pellets, or directly as pellets. The pellets are tempered, to a moisture content of about 25–30%. Afterwards the pellets are compressed into flakes, usually with a hydraulic press or a mechanical fluting roller. The flakes are toasted for a short time, generally several minutes, at temperatures from 100°–220° C. to a final moisture content of less than 3% by weight. Toasting can be accomplished in a conventional oven, or in a continuous fluidized oven.

To fiber fortify pasta, the method comprises adding resistant starch to a traditional pasta dough of flour and water, cold processing the dough in a single screw extruder using standard pasta shaped dies, and drying the dough to a final moisture content of 8.5–11.5%.

Cereal ingredients that are suitable for extrusion processing include, but are not limited to, oat bran, oat flour, wheat bran, wheat flour, unmodified corn starch, corn flour, corn meal, corn bran, rice flour and barley flour. The proportions of the various cereals used in the dough will vary depending on the taste and texture desired in the end product, and these proportions are within the expertise of one skilled in the art. The dough can be flavored and sweetened as desired with such ingredients as sugar, malt, salt, flavor extracts and the like, and suitable dough mixes will have compositions such as those set out in the examples.

The resistant starch is prepared by gelatinizing a slurry of a starch that contains amylose in an amount greater than 40%, treating the gelatinized starch with a debranching enzyme for sufficient time to effect essentially complete debranching, deactivating the enzyme, and isolating the resistant starch product by drying, extrusion, or precipitation by the addition of salt. The starches used in preparing amylase resistant starch may be derived from any source, for example, from corn, potato, sweet potato, wheat, rice, sago, tapioca, waxy maize, and sorghum; however, the preferred starting starch is a starch containing greater than 40% amylose, for example, HYLON V, a corn starch containing about 50% amylose, or HYLON VII, a corn starch containing about 70% amylose, both products of National Starch and Chemical Company, Bridgewater, N.J.

The starting starch is dispersed into an aqueous slurry having a solids content of 5%–40%, preferably about 15%, and heated at sufficient temperature and pressure to effect gelatinization. Although gelatinization may be effected by any of the methods known in the art, the preferred method is to force the starch slurry through a jet cooker in which the starch slurry is contacted with live steam under elevated temperatures. Generally, the conditions for gelatinization are temperatures from 120°–175° C. (250° F.–350° F.), and pressures from 1.05–10.5 kg/cm$^2$ (15–150 psi). Complete gelatinization is desired and is determined visually by the total disintegration of granular structure.

After the starch has been gelatinized, the starch solids content is adjusted to the highest feasible solids level to facilitate subsequent drying of the starch, the preferred solids content being about 15%. A higher solids starch system may be employed if the starch is processed with adequate mixing to uniformly blend enzyme and starch at the higher solids. After the solids content is fixed, the temperature and pH of the starch dispersion are readjusted to provide optimum enzyme activity. These parameters will vary depending upon the type and source of enzyme used, the enzyme concentration, the substrate concentration, and the presence or absence of inhibitors.

A preferred enzyme for enzymatic debranching is pullulanase (E.C. 3.2.1.41; pullulan 6-glucanohydrolase), a heat stable enzyme obtained from a species of Bacillus. Pullulanase will catalyze the hydrolysis of the alpha-1,6 linkages in pullulan and amylopectin, provided that there are at least two glucose units in the side chain. Other endo-alpha-1,6-glucanohydrolases, such as isoamylase (E.C. 3.2. 1.68), or any other endo-enzyme that exhibits selectivity in cleaving the 1,6 linkages of the starch molecule, leaving the 1,4 linkages substantially intact, also may be used to debranch starch according to this method.

When the enzyme used is the Bacillus pullulanase, and the starch solids content is in the range of 5%–35%, the reaction may be carried out in a pH range from 3.0–7.5, preferably from 4.5–5.5, and most preferred at 5.0. Buffers, such as acetates, phosphates, citrates, or the salts of other weak acids can be added to ensure that the pH will be at the optimum level throughout the debranching. At pH 5.0 the preferred temperature for the aqueous starch dispersion during the enzymatic debranching by the Bacillus pullulanase will be between 25°–75° C., the more preferred being between 50°–65° C., and the most preferred being 60° C. As with other parameters of the enzyme reaction, the preferred and optimum temperature ranges will vary with enzyme concentration and source, and substrate concentration and pH, and these can be determined by the practitioner. The pullulanase enzyme is effective at 1500 PUN (pullulanlase units novo/kg starch) using a HYLON V or VII starch substrate at 15% solids content.

The enzymatic treatment is permitted to continue until essentially complete debranching has occurred, which in most systems under optimum enzymatic conditions, will be within 48 hours. The enzyme is deactivated, either by increasing the temperature of the starch dispersion to at least 75° C. for about 15 minutes or by adjusting the pH of the starch dispersion to below 3.0 and holding at that pH for about ½ hour. Bacillus, for example, is rapidly deactivated at temperatures above about 70° C. (158° F.).

The starch is recovered by extrusion, spray drying, flash drying, air drying, freeze drying, vacuum drying, belt drying, drum drying, or any other method known and used in the art for drying and recovering starch. Typical resistant starch content for the recovered starches is in the range of 15–30% by weight. Alternatively, the starch product is recovered by adding an inorganic salt in a minimum of 10%, preferably from 25%–50%, of the solids content to the starch dispersion and incubating the mixture at 50°–100° C., preferably 90°–100° C. Suitable salts are sodium sulfate, ammonium sulfate or magnesium sulfate, and sodium chloride, preferably are the sulfate salts. After the salt incubation, the starch is collected, washed, and dried, and contains a minimum of about 15% resistant starch.

The following examples are illustrative of the invention but are not to be deemed to limit it.

EXAMPLES

Example I

Extruded Expanded Cereal Foods.

Dough compositions: Two basic dough compositions were prepared and their ingredients varied to compare the effects of the addition of oat bran and resistant starch on expansion and total dietary fiber. Basic mix designated "A" in Table 1 consisted by dry weight of 50% corn flour, 10% wheat flour, 10% oat flour, 4% sugar, 1% salt, and 25% oat bran. Variations were prepared by substituting 25% resistant starch (prepared by debranching HYLON VII, a product of National Starch and Chemical Company, Bridgewater, N.J.) for the 25% oat bran.

Basic mix designated "B" in Table 1 consisted by dry weight of 70% oat flour, 20% corn flour and 10% sugar. Variations on dough mix "B" were prepared by substituting 25% oat bran, or 25% resistant starch (prepared by debranching HYLON VII) for 25% of the total oat flour and corn flour. The resistant starch used in the dough mixes was prepared according to the method described above using HYLON VII as the starting starch, and in general, the dough mixes had a total dietary fiber content in the range of 10–15%. Both dough compositions were mixed with water to a final moisture content of 17% by weight.

The oat bran was obtained from National Oats Company; the corn flour from Lincoln Grain as Yellow Corn Flour; the oat flour from Quaker Oats Company.

Each of the dough mix samples was extruded and then measured for expansion and bulk density.

Extruder conditions: Extrusion was performed on a Werner & Pfleiderer Type ZSK-30 twin-screw extruder with a barrel length of 7 (L/D-21). Screw configurations and temperature and time parameters were varied until optimum expansion resulted. The screw configuration was SC 7-20 used with a 3 mm (×2) die. The screws were operated at a speed of 250-350 rpm and the barrel heating zones were set to 60°/60°/150°/140° C. The dry feed rate was 10-13.3 kg/hour.

Tests and results: The dough mixes and the extruded cereals were analyzed for dietary fiber by the Prosky Method for determining dietary fiber in foods, as described in J. Assoc. Off. Anal. Chem., 68,677 (1985). Expansion was measured on 25 samples as the diameter difference between the samples before and after extrusion using dial calipers. The results are reported in centimeters and percentage increase. Bulk density was measured using an Ohaus bulk density scale. The sample containing resistant starch showed an increase in total dietary fiber and in expansion after extrusion compared to a loss of dietary fiber and expansion after extrusion for the original dough mix and for the dough containing oat bran. The results are set out in Table 1.

Example II

Extruded Flaked Cereal Foods.

Dough compositions: Basic dough mix designated "C" in Table 1 consisted by dry weight of 87.2% wheat flakes, 8.7% sugar, 2.4% salt, 1.6% malt syrup (as a liquid at 50% solids), and 0.1% trisodium phosphate. To compare the effects of the addition of oat bran and resistant starch on the texture of extruded flakes and total dietary fiber, a corresponding percentage of the wheat flakes was substituted with either 38% oat bran or 25% resistant starch. A smaller percentage of resistant starch than oat bran was substituted in order to equalize the percentage total dietary fiber in the unextruded dough mix. All the dry ingredients except the wheat flakes were charged into a one gallon jar, capped and set on rollers at 100 rpm for at least three hours to insure sufficient blending. The wheat flakes and malt syrup were introduced into the process separate from the dry blended ingredients. The moisture content was adjusted to 30% by weight.

Extruder conditions and sample preparation: Extrusion was performed on a Werner & Pfleiderer Type ZSK-30 twin screw extruder with a barrel length of 12 (L/D-36). The screw configuration was SC12-44 with a 4 mm (×1) die. The screws were operated at 250 rpm and the barrel heating zones were set to 0°/150°/140° C./cooling water/cooling water. The dry feed rate was 10 kg/hour and the moisture input was 30% by weight. The wheat flakes were fed into the extruder in a separate feeder from the blended dry ingredients. The malt syrup was introduced via a liquid addition pump. Samples 0.64 cm (¼inch) long were collected by cutting the exiting moist pellet (containing 30% moisture). The pellets were then compressed into flakes using a hydraulic press or a cold double drum drier. The pressed flakes were placed on an aluminum baking tray and toasted in a conventional oven at 200-210° C. for 2-7 minutes to a final moisture content of 3-5%.

Tests and results: The dough mixes and the extruded samples were analyzed for dietary fiber by the Prosky Method for determining dietary fiber. The sample containing the resistant starch showed an increase in total dietary fiber after extrusion compared to a loss of dietary fiber after extrusion for the original dough mix and for the mix containing oat bran. The results are set out in Table 1. The samples were also subjectively compared for texture quality, appearance, and bowl life, and the sample containing resistant starch was considered to have superior properties to the original dough mix and the dough mix containing oat bran.

In summary, the results show that the addition of resistant starch to dough mixes to be cooked by extrusion techniques increases the total dietary fiber of the final extruded food product, increases the expansion of extruded cereal products over cereal products without resistant starch or fortified with other forms of dietary fiber, and improves the texture of extruded and flaked cereal products over cereal products that do not contain resistant starch or that are fortified with other forms of dietary fiber.

TABLE 1

| | | Effect of Resistant Starch on Extruded Foods | | | | | |
|---|---|---|---|---|---|---|---|
| | Varied | | | % TDF | | Den- | Expansion | |
| Dough Mix | Ingre- dient | dough | extruded | % change | sity kg/cm³ | cm | % change |
| A | 25% oat bran | 6.6 | 6.1 | −7.6 | (3.65) | 0.89 | |
| | 25% RS* | 10.0 | 13.6 | +36 | (3.60) | 0.88 | |
| B | 0 | 5.8 | 5.8 | 0 | | 0.56 | |
| | 25% oat bran | 8.0 | 7.1 | −21.4 | | 0.40 | −28.6 |
| | 25% RS* | 13.2 | 15.0 | +13.4 | | 0.89 | +58.9 |
| C | 0 | 9 | 8 | 1 | | | |
| | 38% oat bran | 11.1 | 7.6 | −31.5 | | | |
| | 25% RS* | 15.3 | 16.0 | +4.6 | | | |

*RS is resistant starch obtained from debranched HYLON VII.

Example III

Extruded Pasta.

Dough Compositions: A series of pasta dough mixes prepared from Durham wheat flour, or Durham wheat flour in combination with high fiber materials, and water was extruded and tested for total dietary fiber (resistant starch) content and subjective textural properties. The control pasta consisted of all Durham wheat flour and water. The test pastas consisted of 24 parts by weight Durham wheat flour and six parts by weight of a high fiber material selected from the group consisting of resistant starch, oat bran, wheat bran, corn bran, and oat fiber. The amount of water varied with each test dough to between six and nine parts by weight to obtain a workable pasta dough.

Extruder Conditions: Each of the samples was extruded in an Ambrette single screw extruder by cold process using a die with cylindrical void spaces for a ziti shaped pasta. After extrusion, the samples were placed on trays and into a Sargent forced air oven dryer at 43°-46° C. for 2-3 hours to a final moisture level of 8.5-11.5%.

Tests and Results: The extruded samples were analyzed for dietary fiber by the Prosky Method for determining dietary fiber. The results are given in Table 2.

TABLE 2

Pasta Fortifed with Fiber

| Dough | % Moisture in extruded pasta | % Total Dietary Fiber |
| --- | --- | --- |
| Durham wheat | 9.8 | 2.7 |
| Durham wheat with: | | |
| 20% resistant starch | 10.8 | 9.4 |
| 20% oat bran | 11.5 | 4.7 |
| 20% wheat bran | 9.5 | 12.1 |
| 20% corn bran | 9.5 | 19.7 |
| 20% oat fiber | 8.6 | 22.4 |
| 7% oat fiber | 10.2 | 9.6 |

An initial subjective sampling revealed that the pasta containing the corn bran had an unacceptable color and taste, and the pasta containing the oat fibers had a mealy mouthfeel. Therefore, these were eliminated from further panel testing. The samples containing resistant starch, oat bran and wheat bran were subjectively tested for taste and appearance by 21 evaluators. In a comparison of the high fiber substituted pastas, 61.9% of the evaluators found pasta made with the resistant starch the firmest, and 76.2% found pasta made with resistant starch better overall in taste and texture at a 95% confidence level compared to the pastas made with oat bran and wheat bran. In summary, the results show that it is possible to fortify pasta with resistant starch to obtain a higher fiber content without any substantial decrease in taste and texture.

We claim:

1. A method to increase the expansion and improve the texture of extruded food products comprising
   (a) providing an uncooked cereal dough mix,
   (b) adding resistant starch to the cereal dough mix in an amount of 10–25% by weight of the uncooked dough mix,
   (c) adding sufficient water to the cereal dough to attain a moisture content of 14–22% by weight,
   (d) cooking the cereal dough in an extruder, through varied temperature ranges 60°–170° C. at pressures within the range of $2 \times 10^6$–$4.3 \times 10^6$ N/m$^2$ (PA) [having an] to exit a die of a predetermined shape and size at a pressure within the range from $1.38 \times 10^6$–$6.21 \times 10^6$ N/m$^2$ (PA) to yield an expanded dough extrudate, having a moisture content of 8–11% by weight,
   (e) drying the extruded dough to a final moisture content of less than about 3%.

2. The method according to claim 1 in which the uncooked dough comprises ingredients selected from the group consisting of oat bran, oat flour, wheat bran, wheat flour, unmodified corn starch, corn flour, corn meal, corn bran, rice flour and barley flour.

3. A method to improve the texture of extruded food products comprising
   (a) providing an uncooked cereal dough mix,
   (b) adding resistant starch to the cereal dough mix in an amount of 10–25% by weight of the uncooked dough mix,
   (c) adding sufficient water to the cereal dough to attain a moisture content of about 30% by weight,
   (d) cooking the cereal dough in an extruder, through varied temperature ranges of 60°–170° C. at pressures within the range of $1.7 \times 10^6$–$2.2 \times 10^6$ N/m$^2$ (PA) to an exit die of a predetermined shape and size at a pressure within the range from $1.38 \times 10^6$–$6.21 \times 10^6$ N/m$^2$ (PA) to yield pellets of dough extrudate having a moisture content of about 30% by weight,
   (e) tempering the pellets to a moisture content of 25–30% by weight,
   (e) compressing the pellets into flakes, and
   (f) driving the flakes to a final moisture content of less than about 3%.

4. The method according to claim 3 in which the uncooked dough comprises ingredients selected from the group consisting of oat bran, oat flour, wheat bran, wheat flour, unmodified corn starch, corn flour, corn meal, corn bran, rice flour and barley flour.

* * * * *